United States Patent
Walen et al.

(10) Patent No.: US 8,323,285 B2
(45) Date of Patent: Dec. 4, 2012

(54) METHOD FOR MANUFACTURING A SURGICAL SAW BLADE WITH A BLADE HEAD AND RAISED BOSS AROUND WHICH THE BLADE HEAD PIVOTS

(75) Inventors: James G. Walen, Kalamazoo, MI (US); Liam Cosgrove, Clonlara (IE); Robert Brindley, Delton, MI (US)

(73) Assignee: Stryker Ireland, Ltd., Carrigtwohill (IE)

( * ) Notice: Subject to any disclaimer, the term of this patent is extended or adjusted under 35 U.S.C. 154(b) by 756 days.

(21) Appl. No.: 12/389,497

(22) Filed: Feb. 20, 2009

(65) Prior Publication Data
US 2009/0182338 A1   Jul. 16, 2009

Related U.S. Application Data

(63) Continuation of application No. PCT/US2007/076321, filed on Aug. 20, 2007.

(60) Provisional application No. 60/839,051, filed on Aug. 21, 2006.

(51) Int. Cl.
*A61B 17/00* (2006.01)
*B23P 11/00* (2006.01)

(52) U.S. Cl. ............................................ 606/82; 29/428

(58) Field of Classification Search .............. 606/82–85, 606/86 R, 167–179; 29/428
See application file for complete search history.

(56) References Cited

U.S. PATENT DOCUMENTS

| | | | | |
|---|---|---|---|---|
| 5,122,142 A * | 6/1992 | Pascaloff | | 606/82 |
| 5,735,866 A * | 4/1998 | Adams et al. | | 606/178 |
| 6,113,618 A * | 9/2000 | Nic | | 606/176 |
| 6,656,186 B2 * | 12/2003 | Meckel | | 606/82 |
| 6,860,886 B1 * | 3/2005 | Lee | | 606/82 |
| 6,875,222 B2 * | 4/2005 | Long et al. | | 606/172 |
| 7,497,860 B2 * | 3/2009 | Carusillo et al. | | 606/82 |
| 7,691,106 B2 * | 4/2010 | Schenberger et al. | | 606/82 |
| 7,704,254 B2 * | 4/2010 | Walen | | 606/82 |
| 7,998,157 B2 * | 8/2011 | Culp et al. | | 606/170 |
| 8,043,292 B2 * | 10/2011 | Carusillo | | 606/82 |
| 2006/0009796 A1 | 1/2006 | Carusillo et al. | | |

FOREIGN PATENT DOCUMENTS

DE           478354 C    6/1929
WO   WO 2007030793 A    3/2007

OTHER PUBLICATIONS

EPO ISA Search Report and Written Opinion for PCT App. No. PCT/US2007/076321, Jun. 2008.

* cited by examiner

*Primary Examiner* — Kevin T Truong
*Assistant Examiner* — Christopher Beccia

(57) ABSTRACT

In a method of assembling a surgical saw blade assembly with an blade bar that contains an oscillating head, the blade bar is formed from opposed plates. One of the plates is punch stamped to define a boss around which blade head pivots. The plates are secured to one another in a series of steps in which spaced apart sections of the plates are welded together.

22 Claims, 12 Drawing Sheets

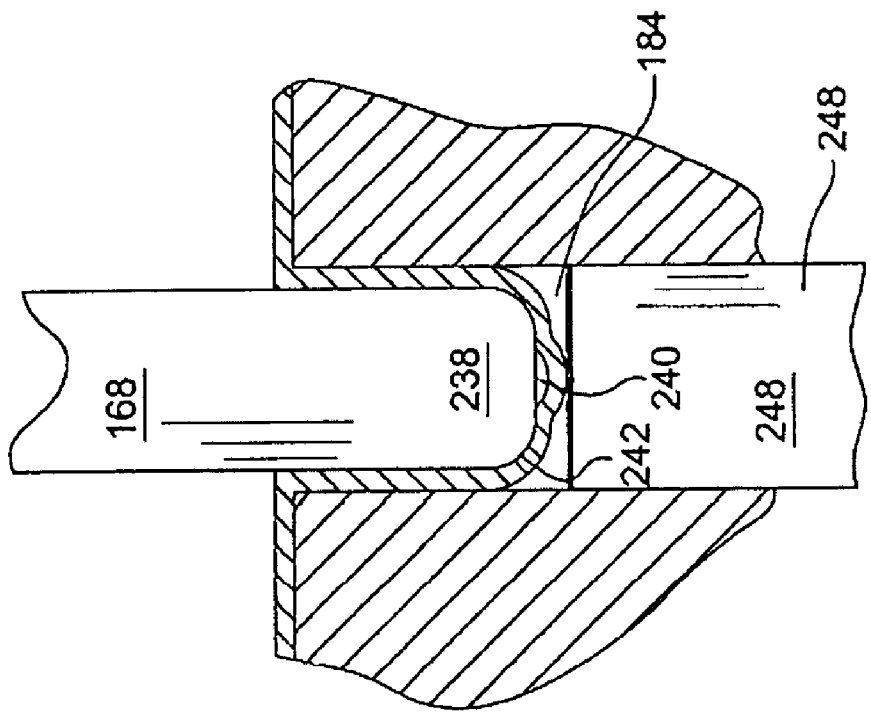
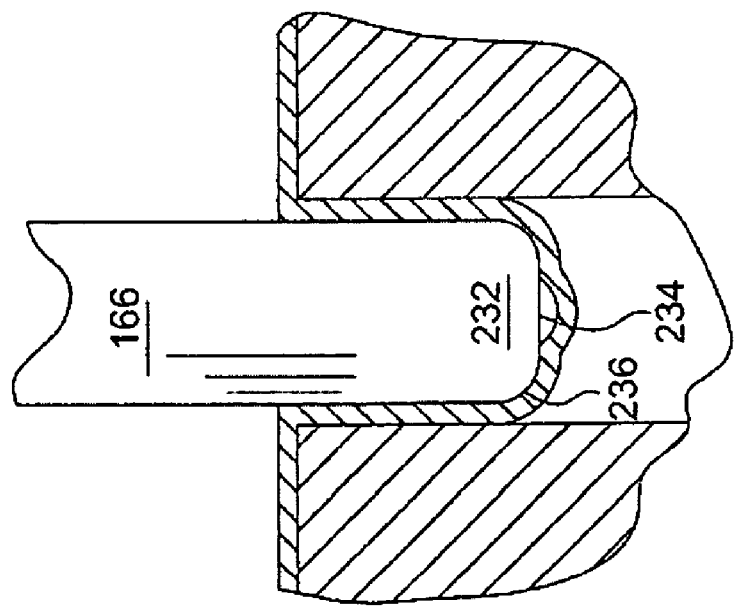

METHOD FOR MANUFACTURING A SURGICAL SAW BLADE WITH A BLADE HEAD AND RAISED BOSS AROUND WHICH THE BLADE HEAD PIVOTS

CROSS-REFERENCE TO RELATED APPLICATIONS

This application is a continuation application of PCT Application No. PCT/US2007/076321, filed 20 Aug. 2007, which claims priority to U.S. Provisional Patent Application No. 60/839,051, filed 21 Aug. 2006, both of which are hereby incorporated by reference in their entireties.

FIELD OF THE INVENTION

This invention relates generally to a method of manufacturing a surgical saw blade that has static blade bar and a head that pivots relative to the blade bar.

BACKGROUND OF THE INVENTION

A sagittal saw blade is a surgical saw with a head that pivots around an axis that is perpendicular to the blade. The United States patent application entitled SURGICAL SAGITTAL SAW WITH INDEXING HEAD AND TOOLLESS BLADE COUPLING ASSEMBLY FOR ACTUATING AN OSCILLATING TIP SAW BLADE AND OSCILLATING TIP SAW BLADE WITH SELF CLEANING HEAD filed 16 Aug. 2006, U.S. Patent Pub. No. US 2007/0119055 A1, the contents of which are incorporated herein by reference, discloses a sagittal saw blade assembly that includes a static blade bar and a blade head. The blade bar is an elongated member that is releasably attached to the handpiece used to actuate the assembly. The blade head is pivotally mounted to the blade bar and has teeth that extend forward from the blade bar. One or more drive links extend from the blade head to the proximal end of the blade bar. The drive links are reciprocated back and forth by a drive assembly internal to the handpiece. The reciprocation of the drive links in turn causes the blade head to pivot back and forth. The pivoting of the blade head is what enables the teeth to cut the tissue against which the blade head is pressed. Generally, this type of blade is known as an oscillating tip saw blade.

An advantage of the oscillating tip saw blade is that the only portion of the blade that pivots is the distally located blade head. In comparison to a conventional sagittal saw blade that pivots from its point of attachment to the complementary handpiece, this blade assembly, when actuated, vibrates less in the hands of the surgeon holding the handpiece. Also, it is common practice to use a cutting guide to properly position a sagittal saw blade relative to the tissue the blade is intended to cut. When a conventional blade is actuated, the oscillating movement of the blade imposes significant wear on the surfaces of the cutting guide defining the slot in which the blade is seated. The blade bar of the oscillating tip blade only minimally moves in this slot. Thus, by using an oscillating tip blade little, if any, of the material forming the cutting guide becomes worn. This reduces the extent to which the surgeon has to flush worn off cutting guide material from the surgical site. Further, use of the oscillating tip blade reduces the extent to which the material forming the guide becomes so worn that the guide itself is rendered useless.

One important component of the above saw blade assembly is the pivot boss. The pivot boss is the cylindrical static member internal to the blade bar against which the blade head both presses and pivots. The outer surface of the blade boss, the surface against which the blade head bears, must be as smooth as possible. This is because surface rough spots will result in wear being concentrated around these points and the complementary surfaces of the blade head that bear against these surfaces. This wear can induce failure in one or both of these components. Even if this wear does not induce structure failure, it can cause an appreciable amount of friction-induced heat to be generated.

The blade bar could be formed by machining a workpiece. In machining, the material forming the workpiece is selectively removed to form the blade bar having the desired geometric features, including the pivot boss. Forming the blade bar using this process can be so expensive that it can be economically impracticable to provide an oscillating tip saw blade.

Furthermore, it is common to form the blade bar of the oscillating tip blade out of opposed upper and lower plates. The blade head and drive rods are sandwiched between the plates. Once these components are assembled together, the opposed plates are secured together to complete the assembly of the oscillating tip blade. Care must be taken in this process to ensure that, post manufacture, the blade bar is as straight as possible. Should the blade bar have any curvature, the blade may bow when pressed against the tissue it is intended to cut. Such curving of the blade can, in turn, result in the blade cutting the tissue along a path that deviates from the intended cut path. This curvature can potentially be so great that it adversely affects the ability of the blade to travel in the slotted cutting guide in which it is inserted.

SUMMARY OF THE INVENTION

This invention is related to a new and useful method of manufacturing an oscillating tip saw blade. In one process of this invention, the blade bar pivot boss is progressively formed in one of the plates forming the pivot boss. Then, the plates forming the blade bar are welded in a selected pattern to substantially eliminate the deformation of the plates due to the welding process.

In one process of this invention, the first step in formation of the pivot boss comprises punch forming a relatively deep bullet shaped node in the plate in which the pivot boss is to be formed. Then, in a set of additional sequential punching steps, the node is widened to provide it with an outer cylindrical profile. In the latter punching processes, the head of the node is progressively flattened to create the desired final pivot boss.

The above process creates a pivot boss with a cylindrical geometry and does not excessively mar the surface finish of the bar material forming the geometry.

Once the blade head and drive rods are sandwiched between the plates forming the blade bar, the plates are welded together. More particularly the plates are welded together using a laser welding process. In this process, gussets from a first one of plates that abut the second plate are penetration welded to the second plate. Then the outer perimeters of the plates are welded together. Each welding process comprises a number of separate welding steps. In the individual welding steps, sections of the plates are subjected to closely spaced spot welding. The individual sections are spaced apart from each other. Thus, after welding is completed between one section of adjoining plates, the next section at which the welding occurs is spaced from the initial section.

The above welding process minimizes the extent to which any individual section of the bar-forming plates is heated. This reduces the deformation of the material forming the plates. The reduction of this deformation results in a like minimization of the extent to which the blade bar, in the process of its formation, becomes bowed.

BRIEF DESCRIPTION OF THE DRAWINGS

The above and further features and benefits of this invention are understood from the Detailed Description below taken in conjunction with the attached drawings in which:

FIG. 7 is a side and partial cross sectional view of how the third punch continues the process of the pivot boss formation;

FIG. 8 is a side and partial cross sectional view of how the fourth punch continues the process of the pivot boss formation;

It should be appreciated that the above drawings, which illustrate mechanical elements of this invention, should be understood to generally show the relative proportions of the individual features of the element components and of the elements to each other. Drawings in which features are exaggerated for ease of illustration are identified

DETAILED DESCRIPTION

Figure 1:
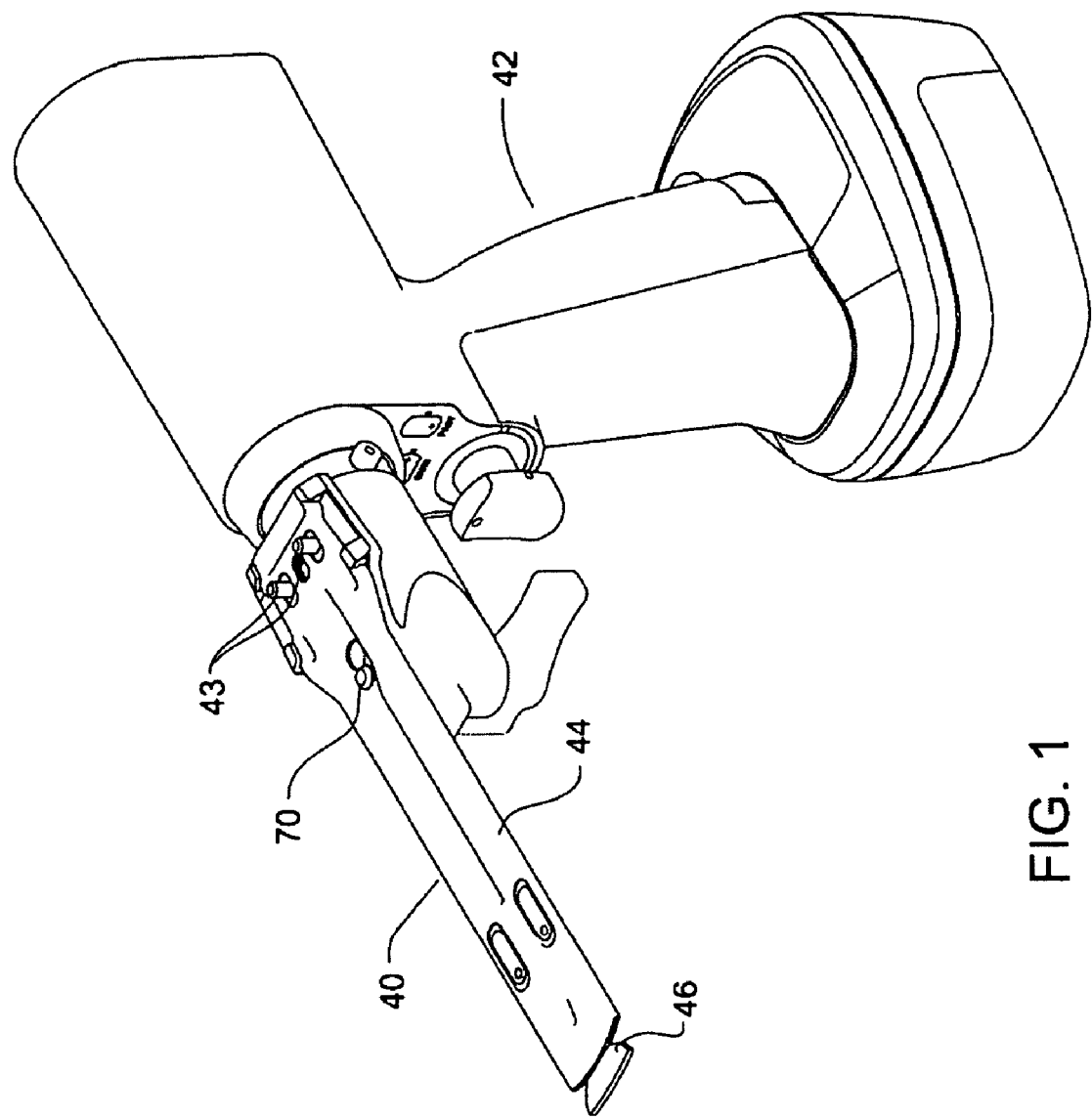
FIG. 1 is a perspective view of a oscillating tip saw blade of this invention is attached to a handpiece.
Figure 2:
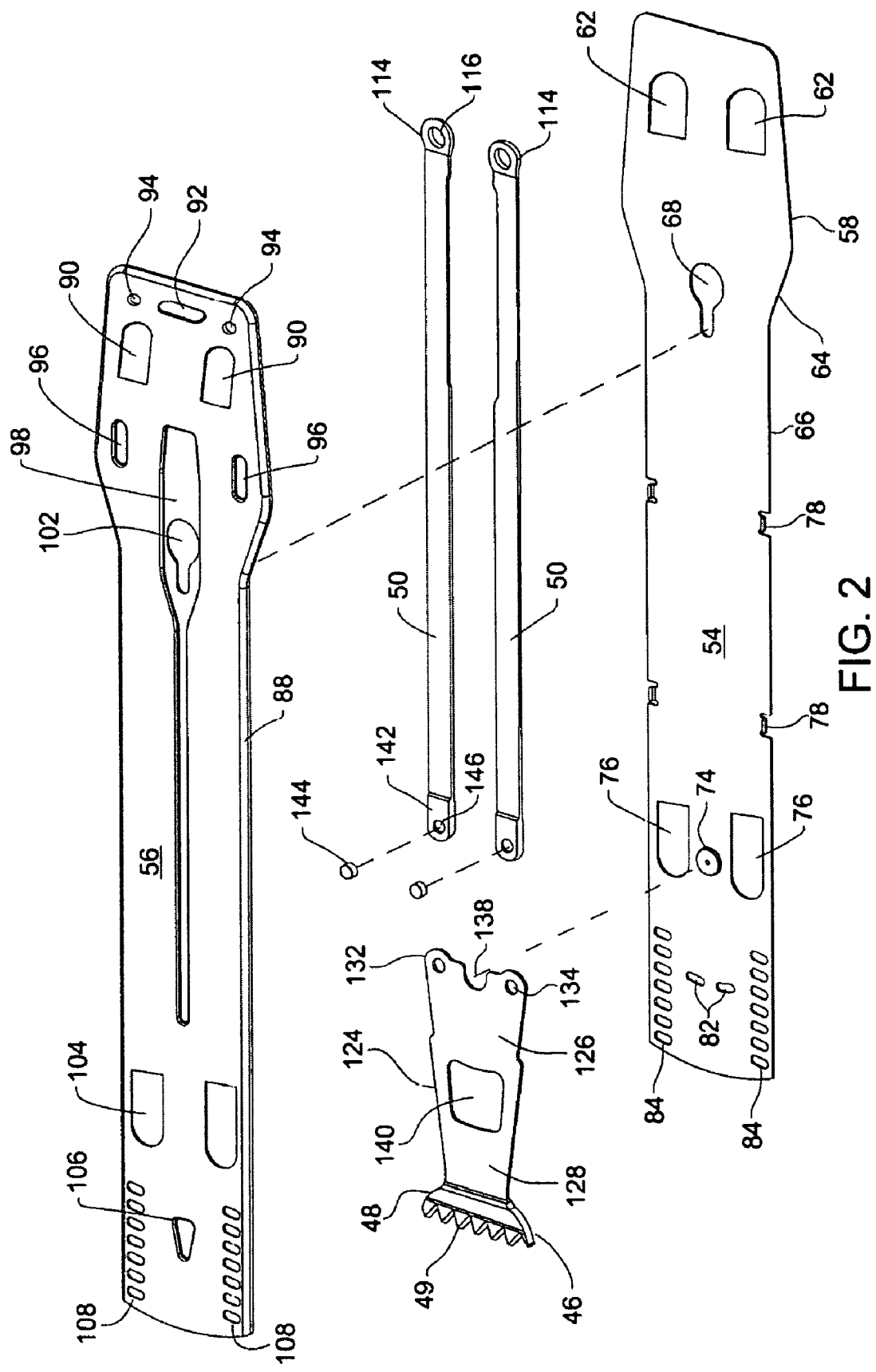
FIG. 2 is an exploded view of the oscillating tip saw blade.

FIGS. 1 and 2 depict a saw blade assembly 40 constructed in accordance with this invention attached to a handpiece 42. Saw blade assembly 40 includes a blade bar 44 that is removably attached to the distal end of the handpiece 42. ("Distal" means away from the surgeon, i.e., towards the surgical site to which the assembly is applied. "Proximal" means towards the surgeon, i.e., away from the surgical site.) A blade head 46 is disposed in and pivotally mounted to the blade bar 44. The blade head 46 has a crown 48 located forward of the blade bar 44. The crown 48 is formed with cutting teeth 49. Drive rods 50 disposed in the blade bar 44 extend proximally rearward from the blade head 46. Drive rods 50 are releaseably connected to an oscillating drive mechanism, internal to the handpiece (drive mechanism not illustrated and not part of this invention). As a consequence of the actuation of the drive mechanism, the drive rods 50 reciprocate back and forth along the longitudinal axis of the blade bar. The reciprocation of the drive rods 50 causes blade head 46 to pivot.

Blade bar 44 is formed from lower and upper plates 54 and 56, respectively. The lower plate 54 has a proximally located base 58, generally in the form of trapezoid, in which the opposed lateral side edges are symmetric and taper inwardly towards the proximal end edge of the plate 54. Lower plate base 58 is further formed to have two D-shaped openings 62. The longitudinal axes of openings 62 are symmetrically spaced from and parallel with the longitudinal axis of the lower plate 54.

Forward of the base 58, the lower plate 54 is formed to have an intermediate section 64. The side edges of intermediate section 64 taper inwardly as they extend distally forward. Plate intermediate section 64 transitions into a constant width blade distal section 66. The lower plate 54 is further formed so as to define a keyhole-shaped opening 68 that extends from the intermediate section 62 to the distal section 66. Opening 68 is dimensioned to receiving a coupling pin 70 that is part of the handpiece 42. Coupling pin 70 is part of the handpiece components that releasably holds the blade bar 44 to the handpiece.

The forward portion of the bar lower plate distal section 66 is formed with a circular, upwardly extending boss 74. On either side of boss 74, lower plate 54 defines a D-shaped opening 76. Each opening 76 is longitudinally aligned with a separate one of the openings 62. Lower plate 54 is also formed to have two pairs of L-shaped tabs 78. Each tab 78 is located immediately inward of the adjacent longitudinal side of the lower plate 54. Each tab 78 extends upwardly towards the upper plate 56. Tabs 78 are arranged in pairs such that one tab of each pair is diametrically opposed to the second tab of the pair. A first pair of tabs 78 is located along a line perpendicular to the longitudinal axis of the lower plate distal to opening 68. The second pair of tabs 78 is located along a line between the first set of tabs 78 and openings 76.

Forward of openings 76, the lower plate 54 is formed with two additional openings, discharge ports 82. More particularly, the discharge ports 82 open from a section of the surface of the lower plate that is subtended by the blade head base 124. Each discharge port 82 is approximately in the shape of an oval. Lower plate 54 is further formed so that the discharge ports 82 are centered on a common non-linear longitudinal axis. More particularly this axis is curved. The radius of curvature of this axis is center in which the section of the blade head 46 disposed underneath the ports oscillates. Discharge ports 82 are symmetrically located around the longitudinal axis of the lower plate 54.

Two rows of oval shaped openings 84 are also formed in the lower plate 54. Each row of openings 84 is located immediately inward one of the side edges of the lower plate 54. Each row of openings starts with an opening located immediately proximal to the distal end edge of the lower plate 54 and extends proximally rearward from that distal most opening 84. Each row of openings 84 extends a short distance proximally rearward from the adjacent discharge port 82.

The upper plate 56 is shaped to have the same general perimeter profile of the lower plate 54. The description of this profile is not repeated. Upper plate 56 is further formed to have a lip 88 that extends downwardly from the edges of the upper plate. Collectively, the plates 54 and 56 are dimensioned so that when the upper plate 56 is disposed over the lower plate 54, the upper plate lip 88 extends around the adjacent edges of the lower plate 54. The upper plate 56 is formed so that lip 88 extends around the proximal end of the lower plate 54 and the opposed longitudinally extending side edges of the lower plate 54. Thus, upon assembly, blade bar 44 has a distal end opening between the lower plate 54 and the upper plate 56 (opening not identified).

Upper plate 56 is further formed to have two D-shaped openings 90. Each opening 90 is identical in shape with and positioned to be aligned directly over one of the lower plate openings 62. Located proximally rearward of openings 90, upper plate 56 is further formed to have a downwardly extending gusset 92. Gusset 92 extends laterally across upper plate 56 at a location immediately forward of the proximal end of the plate. Two small downwardly extending gussets 94 are located on either side of gusset 92

Forward of openings 90, the upper plate 56 is formed with two gussets 96 and a single gusset 98. Gussets 96 are symmetrically located around the longitudinal axis of the upper plate 56. The gussets 96 are located in the lateral slice section of the upper plate 56 that has the greatest width along the upper plate. Each gusset 96 is located immediately inside the outer perimeter section of the upper plate 56 that transitions into lip 88. Gussets 96 are oval shaped.

Upper plate 56 is formed so that gusset 98 is centered and extends along the longitudinal axis of the upper plate. Gusset 98 extends from a position slightly proximal to the proximal ends of gussets 96 to a position approximately equal to the proximal ends of below discussed openings 104. The upper plate 56 is shaped so that, adjacent gussets 96, gusset 98 is relatively wide. ("Wide" and "narrow" with respect to gusset 98 refers to the width of the gusset along its lateral axis.) Forward of the proximal end of the gusset 98, a key hole shaped opening 102 is formed in gusset 98. Opening 102 is identical in size and is positioned to be aligned with lower plate opening 68. Distally forward of opening 102, the upper plate 56 is formed so that gusset 98 has a constant, narrow width.

A pair of additional D-shaped openings 104 extends through the distal end of the upper plate 56. Each opening 104 has the same shape and is aligned with a complementary underling lower plate opening 76. Forward of openings 104, upper plate 56 is further formed to have a triangularly shaped gusset 106. Gusset 106 is centered on the longitudinal center line of the upper plate. Gusset 106 is further positioned to extend from an interior surface of the upper plate within the area of the surface that is subtended by the blade head base 124.

Upper plate 56 is further formed to have two rows of oval-shaped openings 108. Each row of openings 108 is located adjacent a side edge of the upper plate. Each row of openings 108, like lower plate openings 84, extends proximally rearward from the distal end of the upper plate. Lower plate openings 84 and upper plate openings 108 may or may not overlap with each other.

Drive rods 50 are disposed between the blade bar lower and upper plates 54 and 56, respectively. Each drive rod 50 is in the form of an elongated flat strip of metal. The drive rods 50 are formed so that, at the proximal end of each rod, there is a circular foot 114. Each foot 114 is formed to have a center located through hole 116. Through holes 116 are dimensioned so that the associated drive rod feet 114 can be fitted to drive pins 43 integral with the handpiece 42.

It should be appreciated that the drive rods 50 are formed so that their feet 114 have a thickness greater than that of the elongated center body. In some versions of the invention, the basic thickness of the drive rod 50 is approximately 0.38 mm (0.015 inches); the reinforcing rings around the hole 116 provide this section with the rod with a thickness of approximately 1.14 mm (0.045 inches). In some versions of the invention, the drive rod 50 is so shaped by the selectively grinding of the workpiece from which the drive rod is formed.

The blade head 46, has a base 124, which is the portion of the blade head from which the crown 48 extends. The blade head is seated in the gap between lower and upper plates 54 and 56, respectively. In one version of the invention, the blade head base has a thickness of approximately 0.025 mm (0.001 inches) less than the width of the gap between the opposed faces of the lower and upper plates 54 and 56, respectively. Blade head base 124 is shaped so as to have both a proximal section 126 and an adjacent distal section 128. While not identified, it can be seen that extending forwardly from the proximal end of the proximal section 126, the side edges of the blade base taper inwardly. Blade base distal section 128 has a proximal end that extends outwardly from the adjacent narrow end of the proximal section 126.

Blade base 124 is further formed so that adjacent the proximal section 126, at the proximal end of the blade base 124, there is a pair of opposed feet 132. Each foot 132 is arcuately shaped. Diametrically opposed through holes 134 are further formed in blade head base 124 immediately forward of the proximal end. Each through hole 134 is centered on axis around which the adjacent foot 132 is centered. The distal end of the blade head base 124 is further formed to define a concave semi-circular notch 138. Notch 138 is centered along the longitudinal axis of the blade head 46. More particularly, notch 138 is dimensioned so that when saw blade assembly 40 is assembled, lower plate boss 74 seats in the notch 138 and blade head 46 is able to pivot around the boss.

Blade head base distal section 128 has two side edges (not identified) that, extending distally along the blade head 46, taper inwardly. Base distal section 128 is further formed to define a through window 140. Window 140 is positioned so that when the saw blade assembly 40 is assembled, upper plate gusset 106 extends through the window 140.

The blade head crown 48 has a thickness greater than that of the associated base 124. More particularly, blade head crown 48 is formed so that the kerf cut by the crown is sufficiently wide to allow the insertion of the blade bar 44 into the kerf. Often the crown is formed so that the kerf is at least 0.025 mm (0.001 inches) greater than the thickness of the blade bar 44. The exact geometry of the blade head crown 48 is a function of the particular kerf geometry and not otherwise relevant to this invention. Fingers 142 and pins 144 pivotally hold the blade head 46 to the drive rods 50. A pair of fingers 142 extends forward from the distal end surfaces of each drive rod 50. Fingers 142 are integrally formed with the drive rods 50. Each drive rod 50 is surface ground to form the narrow thickness elongated body and a relatively wider distal end. A cutting process such as a wire electrical discharge machining process is used to form the finger-separating kerf in which the blade head base 124 is slip fitted. During the surface grinding process, each drive rod 50 is further formed to define the relatively thick feet 114.

Each finger 142 is formed with a through hole 146. When saw blade assembly 40 is assembled, pins 144 extend through finger holes 146 and blade base holes 134 to pivotally hold the blade head 46 to the drive rods 50. In some versions of the invention, pins 144 are formed from a stainless steel, such as stainless steel Material Type EN100-3 1.4034 or 400 Series stainless steel.

Often the pins 144 are secured in place by a laser welding process. This is a two-step process. In the first step of the process, the outer circular edge at one end of the pin 144 is laser welded to the adjacent edge of the drive rod finger 142 that defines the hole 146 in which the pin is seated. Then, in a second step of the process, the opposed end of the pin is laser welded to the adjacent edge surface of the opposite finger 142.

Once the blade head and drive rod sub-assembly is fabricated, this sub-assembly is placed against the inner surface of the upper plate 56. The lower plate 54 is fitted within the upper plate lip 88. As a result of this arrangement, the relatively thick drive rod feet are disposed within the lower and upper plate openings 62 and 90, respectively. Fingers 142 and pins 144 are disposed in the lower and upper plate openings 76 and 104, respectively.

Figure 3:
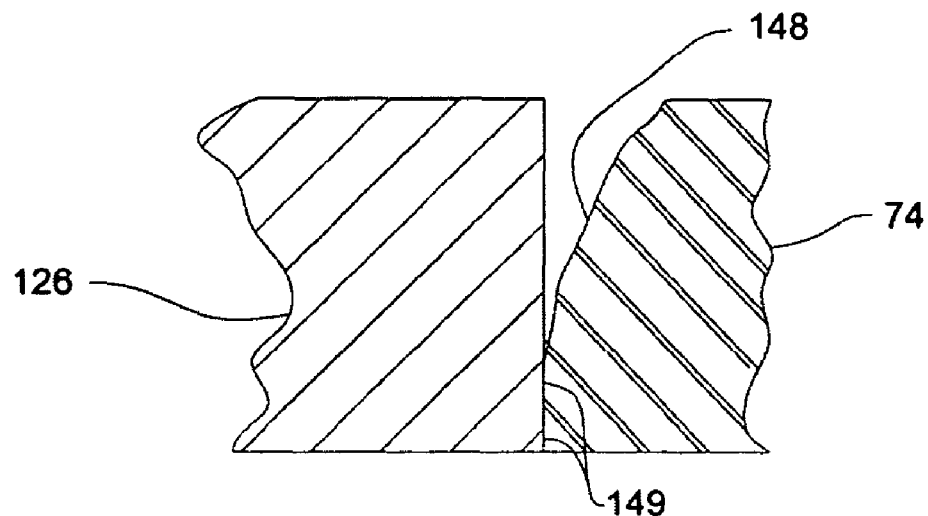
FIG. 3 is a cross sectional exaggerated view of the problem area that can be present if the pivot boss of the blade bar does not have a cylindrical profile.

When the saw blade assembly 40 is fitted to the handpiece 42, the drive pins 43 integral with the handpiece and the drive rods 50 cooperate to pull the blade head base 124 against blade bar boss 74. During actuation of the saw blade assembly 40, the concave surface of the blade head 46 that defines notch 138 is thus pivoted back and forth against boss 74. FIG. 3 is an exaggerated view of what happens if the circumferential surface of the boss 74 against which the blade head base 124 abuts is not essentially cylindrical. Specifically, if due to imprecise manufacturing methods, the surface of the boss tapers proximally away from the notch defining surface of the blade head base 124. In FIG. 3, this taper, called out by identification number 148, is exaggerated for purposes of illustration. Specifically, in this event, the force the blade head base 124 exerts on the boss 74 is distributed over a relatively narrow area, called out by identification number 149. This means that this area is subjected to appreciable mechanical stress and friction induced heat. Consequently, these two concentrated forms of energy can potentially cause the material forming the boss to fail.

Figure 4:
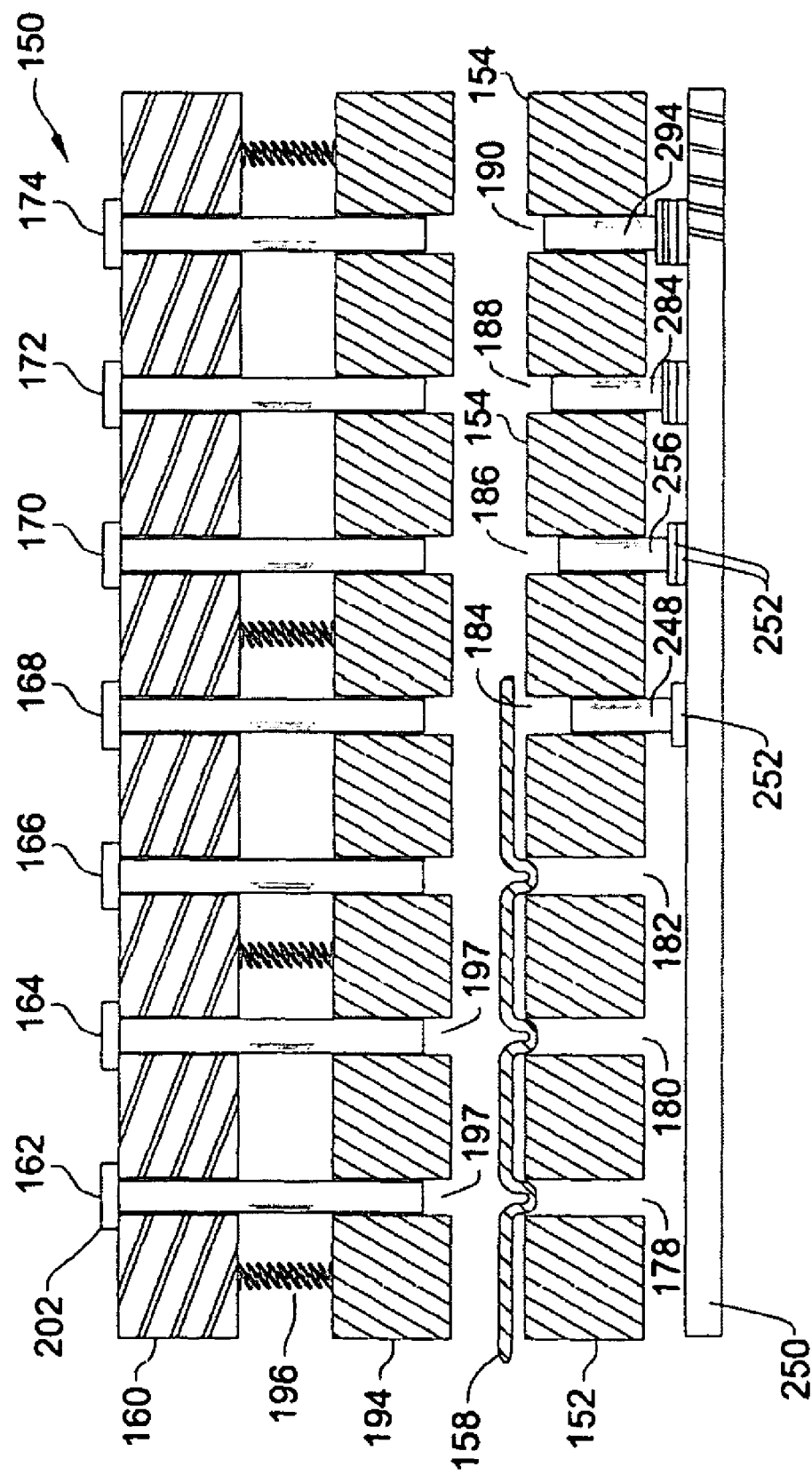
FIG. 4 is a diagrammatic illustration of the press used to form the blade bar according to this invention.

A method of manufacturing the lower plate 54 so as to produce a pivot boss that is relatively cylindrical is now initially described by reference to FIG. 4. Specifically in a sequence of punch steps, the pivot boss 74 is formed in the lower plate. In FIG. 4, a progressive metal press 150 for performing these steps is illustrated. Press 150 has a lower die plate 152 that is static. Lower die plate 152 has an exposed top surface 154. Die plate top surface 154 is the surface over which a metal ribbon 158 from which a number of lower plates 54 are successively formed. An upper punch plate 160 is positioned above lower die plate top surface 154. A number of punches 162-174 are suspended from the upper punch plate 160 and are directed toward the lower die plate 152. Below each punch 162-174, the lower die plate 152 is formed with a number of bores 178-190, respectively. Each location where there is a punch-bore pair can be considered a separate punch station on the press 150.

Metal press 150 also includes a platen 194. Platen 194 extends below the upper punch plate 160 and is suspended from the upper punch plate by a set of springs 196. The platen 194 is formed with a number of through holes 197. Each punch 162-174 is seated in a separate one of the platen through holes 197.

Not illustrated, but understood to be part of the metal press 150, is the drive mechanism that forces the upper punch plate 160, punches 162-174, and platen 194 against the metal ribbon 158 under underlying die plate 152. In some versions of this invention, the drive mechanism can force the upper punch plate 160 against the die plate with between 227 metric tonnes (250 British tons) and 454 metric tonnes (500 British tons) of force. In some versions of the invention, the drive mechanism forces the upper punch plate against the lower die plate with a minimum of 90 metric tonnes (a minimum of 99 British tons) of force.

Also not shown is the transfer mechanism attached to the metal press 150. The transfer mechanism moves the metal ribbon 158 in a step pattern between each of the seven punch stations. Thus, in each operation of the press 150, a punch step is performed on seven different sections of the metal ribbon. After each ribbon section is subjected to the seventh step, the pivot boss 74 can be considered completely formed. After this seventh step, each lower plate-forming section of the metal ribbon 158 can be subjected to additional press operations. These punch operations are not relevant to the formation of the boss 74.

In some preferred versions of the invention, the metal ribbon 158, from which lower and upper plates 54 and 56 is formed, is from 420 stainless steel or equivalent metal. One such metal is the Sandvik 7C27Mo2 strip steel available from Sandvik AB of Sandviken, Sweden. This material is understood to have a chemical composition by weight of 0.38% Carbon, 0.40% Silicon, 0.55% Manganese, 0.025% Max Phosphorus, 0.010% Max Sulfur, 13.5% Chromium, Balance Iron. The thickness of the metal ribbon 158 is 0.38 mm (0.015 inches) or less.

Each time the metal press is actuated, platen 194 presses against the metal ribbon 158. The platen 194 compresses against the metal ribbon 158 to hold the metal ribbon to the die plate top surface 154. As the upper punch plate 160 continues to move downwardly, each punch 162-174 extends through the associated platen through hole 197. The punches then press against the underlying section of the metal ribbon trapped and accessible at the punch station. Each punch 162-174 then forces the underlying metal into the associated die plate bore 178-190, respectively. This successive punch shaping of the metal ribbon results in the pivot boss 74 being formed with the desired cylindrical geometry.

Figure 5:
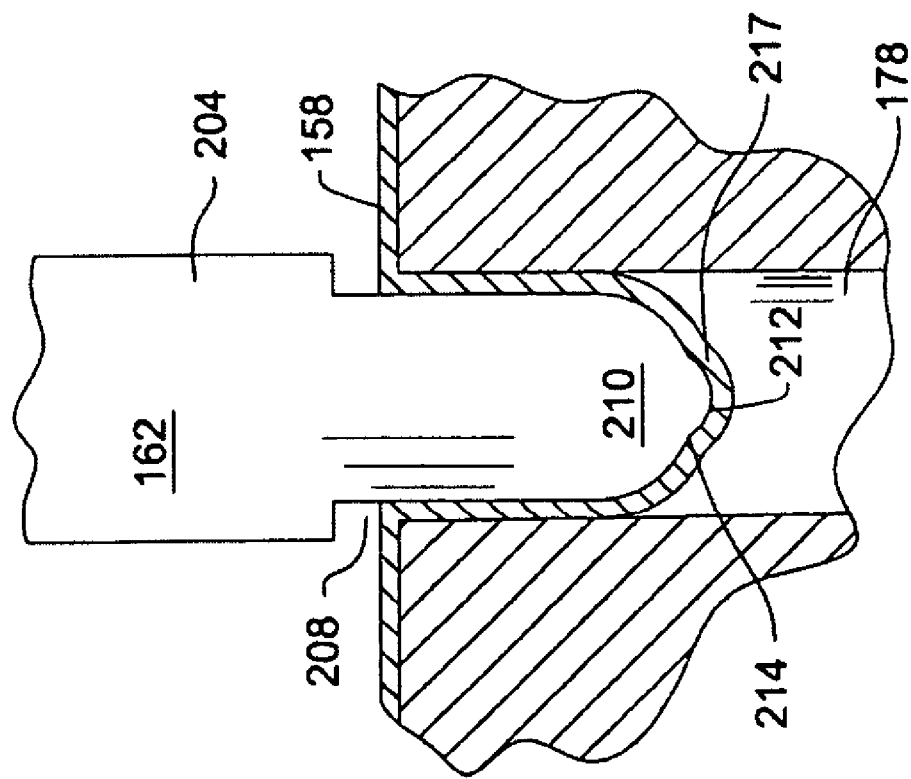
FIG. 5 is a side and partial cross sectional view of how the first punch starts the process of the pivot boss formation.
Figure 9:
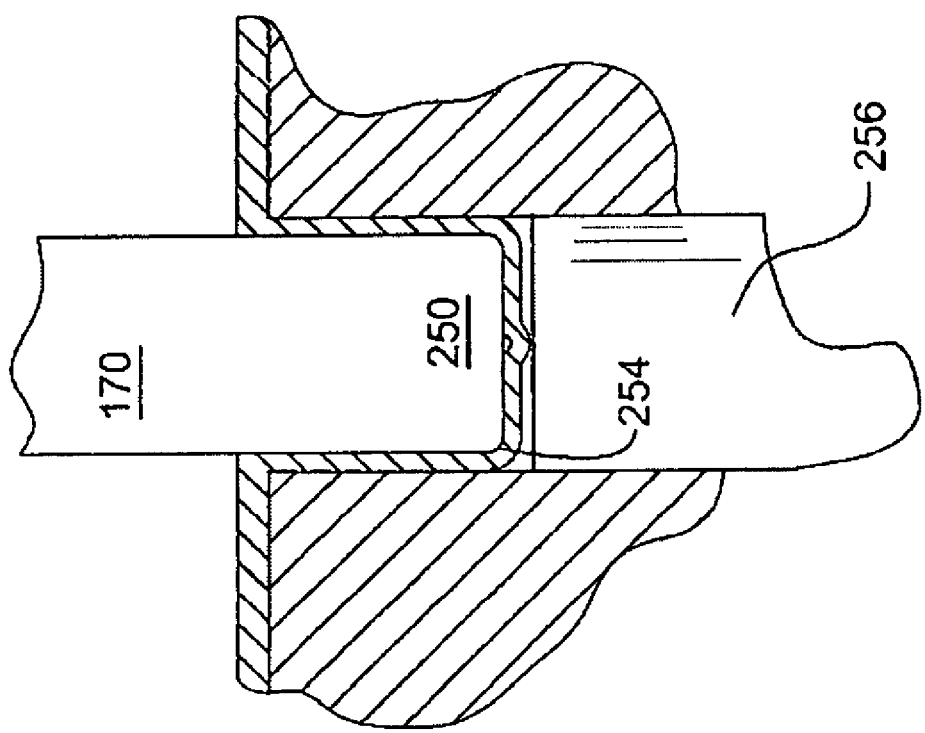
FIG. 9 is a side and partial cross sectional view of how the fifth punch continues the process of the pivot boss formation.

FIG. 5 illustrates how in the first punch step punch 162 starts to form the pivot boss 74. Punch 162, as do the remaining punches 164-174, has a wide diameter base (not illustrated). The base is shaped to facilitate the close sliding movement of the punch in the associated platen through hole 197. A narrow diameter elongated stem 204 extends downwardly from the base. A head, which may be narrower than the stem 204, extends below the stem. The head of punch 162 is shaped to define a cylindrical pedestal 208. Pedestal 208 has a diameter less than that of the associated stem 204. Below pedestal 208, punch 162 has a tip 210. Tip 210 is the portion of punch 162 that strikes the underlying metal ribbon 158. Tip 210 has a bullet shaped profile. Thus, tip 210 has a center surface 212 with a first, narrow diameter radius of curvature. Tip 210 also has a perimeter surface 214 that extends between center surface 212 and the outer perimeter of head pedestal 208. Perimeter surface 214 has a radius of curvature greater than that of the center surface 212. While the radii of curvature of surfaces 212 and 214 are different, both curves are centered on the longitudinal center line of the punch 162. The center of curvature of the center surface 212 is closer to the end of the punch 162 then the center of curvature of surface 214.

In this punching step, the head of punch 162 drives the previously flat section of metal ribbon into the underlying die plate bore 178. Thus, as a consequence of this step, the metal ribbon now has bullet nosed shaped boss, called out by identification number 217.

In between the first and second punching step, the section of the metal ribbon 158 in which bullet nose shaped boss is formed is transferred to the punch station at which the second punch, punch 164, is located. It should be understood that a similar transfer takes place after each punch step. These additional transfer steps will not be discussed further.

The second through seventh punches 164-174 reshape the boss 74 so it has the designed cylindrical shape. Second punch 164, shown best in FIG. 6, has a stem 217 from which a cylindrical pedestal 218 with a diameter less than that of stem 217 extends. Pedestal is shaped to have a rounded tip 220. Pedestal 218 of second punch 164 is wider in diameter than pedestal 208 of first punch 162. Tip 220 is shaped to have a center surface 222 that is rounded and that has a first radius of curvature. Between center surface 222 and pedestal 214, tip 220 has a perimeter surface 224. The perimeter surface 224 has a lager radius of curvature than that of center section 222. Thus, along any lateral line through second punch tip 220, center surface 222 has a radius of curvature centered at a point along the longitudinal axis through the punch 164. At the opposed ends of tip 220, the perimeter surface 224 has two radii of curvature that are located on opposed sides of the longitudinal axis.

Figure 6:
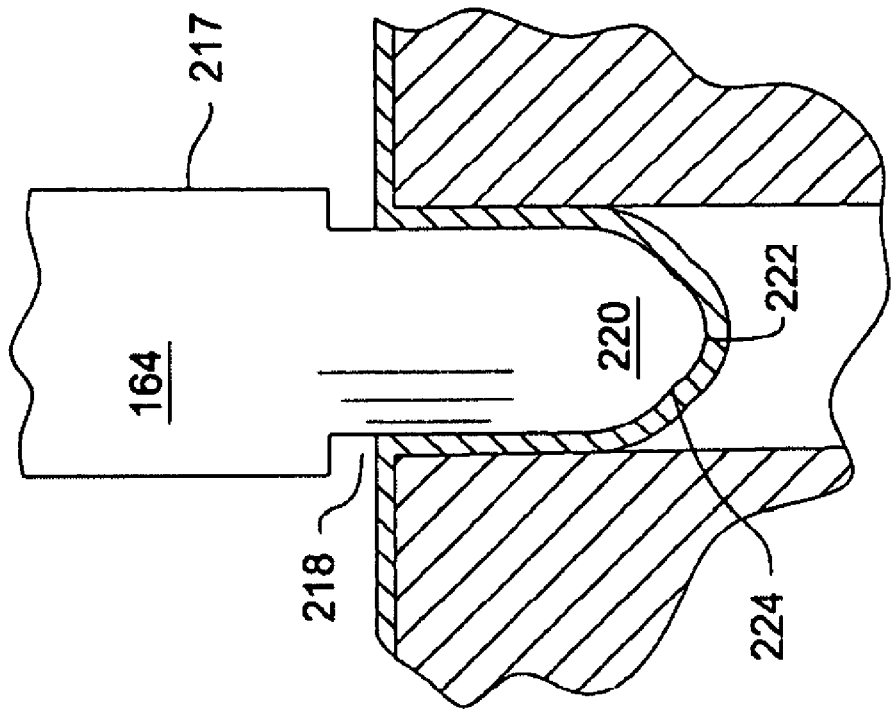
FIG. 6 is a side and partial cross sectional view of how the second punch continues the process of the pivot boss formation.

Also it should be understood that the overall length of the second punch 164 from the free end of the base 202 to the opposed end of the tip center section 222 is shorter than the comparable length of first punch 162. In FIG. 4, the differences in these lengths are exaggerated for purposes of illustration. Thus, as seen in FIG. 6, as a result of the second punching step, the end of the boss, in comparison to the shape of the first step, develops an end that is less rounded and a transition section immediately above the end that is less curved, more angled.

FIG. 7 illustrates the third punch, punch 166, and the shape of the boss as a result of its deformation by this punch. Specifically, third punch 166 has a tip 232 with a generally cylindrical shape. The diameter of tip 232 is greater than that of the pedestal 218 of the second punch 164. Tip 232 has an outer face 234 that is planar. Between outer face 234 and the cylindrical side wall, tip 232 has a curved corner 236. The radius of curvature of corner 236 is less than the radius of curvature of the second punch tip perimeter surface 224.

The overall length of third punch 166 is less than the overall length of the second punch 164. Punch 166, as well as remaining punches 168-174, are shaped so as not to have intermediate stem sections located between their bases and metal shaping heads.

Consequently, as a result of the third punching step, the end of the boss under formation continues to develop a more planar shape. Also the annular section of the boss adjacent the top of the boss, (shown inverted in FIG. 7) is pressed into a more cylindrical shape. Further, as a result of the outward deformation of the material forming the boss, the overall height of the boss, relative to its earlier shape, starts to decrease.

Fourth punch 168, seen in FIG. 8, has a tip 238 with the same basic geometry as the tip 232 of the third punch 166. Tip 238 has the same outer diameter as tip 232. Tip 238 also has a flat outer face 240. Between the outer face 240 and the cylindrically perimeter surface, tip 238 has a curved corner 242. Corner 242 has a radius of curvature less than that of corner 236 of the third punch 166. The fourth punch 168 has an overall length that is slightly less than that of the third punch 166.

Die plate bore 184, the bore in which the fourth punch 168 presses the boss under formation is not totally open. Bore 184, like the remaining bores 186, 188 and 190, is fitted with a plug 248. The plug 248, as seen in FIG. 4, is seated on a base plate 250 located below the die plate 152. In practice, plug 248 rests on shims 252, a single one shown that rests on the base plate. Shims 252 are selectively removed and replaced to regulate the relative position of the head of the plug to the die plate top surface 154. It should be appreciated that the shims are similarly used to position the plugs 256, 284, 294 in bores 186, 188 and 190, respectively.

Plug 248 is positioned in bore 184 so that when the boss under formation is initially seated in the bore, the tip of the bore rests on the exposed top surface of the plug. When the upper punch plate 160 is lowered, platen 194 holds the partially formed boss against plug 248. Fourth punch 168 then presses against the inner surface of the metal forming the boss. Thus, the end of the boss is sandwiched between the top of the plug 248 and the punch tip 238. As a consequence of this action, the extent to which the top of the boss takes on a planar shape increases, i.e., the top of the boss flattens. Also, the extent to which transition between the annular side wall of the boss and its top surface takes on the profile of a perpendicular angle increases, i.e., becomes less rounded.

Fifth punch 170 has a tip 252 very similar to the fourth punch tip 238. The outer diameters of the tips are the same. A difference between the tips is that tip 252 has a corner 254 with a radius of curvature that is less than the radius of curvature of the corner of tip 238 (the transition is more angular). Fifth punch 170 is shorter than fourth punch 168. A plug 256 is seated in the die press bore 186, the bore in which punch 170 is inserted. Plug 256 is positioned in bore 186, so that tip of the plug, the end in the bore, is closer to the die plate top surface 154 than the tip of plug 248.

Thus, in this punch step, punch tip 252 presses the boss under formation against plug 256. This action further flattens the boss and increases the extent to which it has a cylindrical shape.

The sixth and seventh punch steps are similar to the fourth and fifth punch steps. However, the sixth punch 172 has a tip 280 with a diameter slightly less than that of fifth punch tip 252. Sixth punch tip 280 has a corner surface 282 with a radius of curvature less than that of corner surface 254 of the fifth punch 170. The overall length of the sixth punch 172 is less than that of the fifth punch 170.

A plug 284 is seated in die plate bore 188, the bore into which the sixth punch 172 extends. Shims 252 hold the plug in the bore 188 so that the tip 280 of the plug is closer to the die plate top surface 154 than the tip of plug 256.

The seventh punch step is the final process in the formation of pivot boss 74. Seventh punch 174 has a tip 290 with a diameter equal to the diameter of fifth punch tip 252. Punch tip 290 has a corner 292 with a radius of curvature equal to radius curvature of sixth punch corner surface 282. The seventh punch 174 is slightly shorter than the sixth punch 172.

A plug 294 is formed in the die plate bore 190 into which the seventh punch 174 extends. Plug 294 is positioned in the bore 190 so that the plug tip 290 is, in comparison to the tip of plug 284, closer to the die plate top surface 154.

Figure 11:
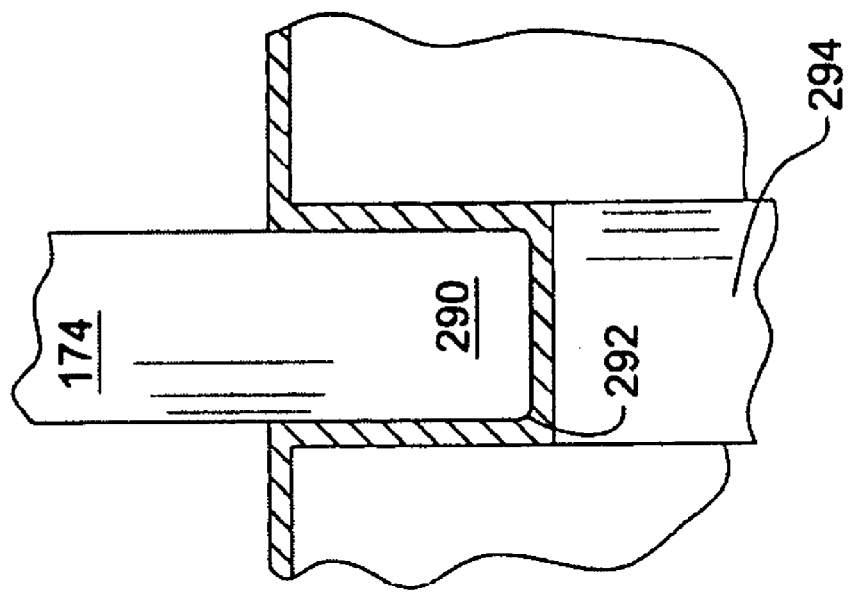
FIG. 11 is a side and partial cross sectional view of how the seventh punch completes the process of the pivot boss formation.
Figure 10:
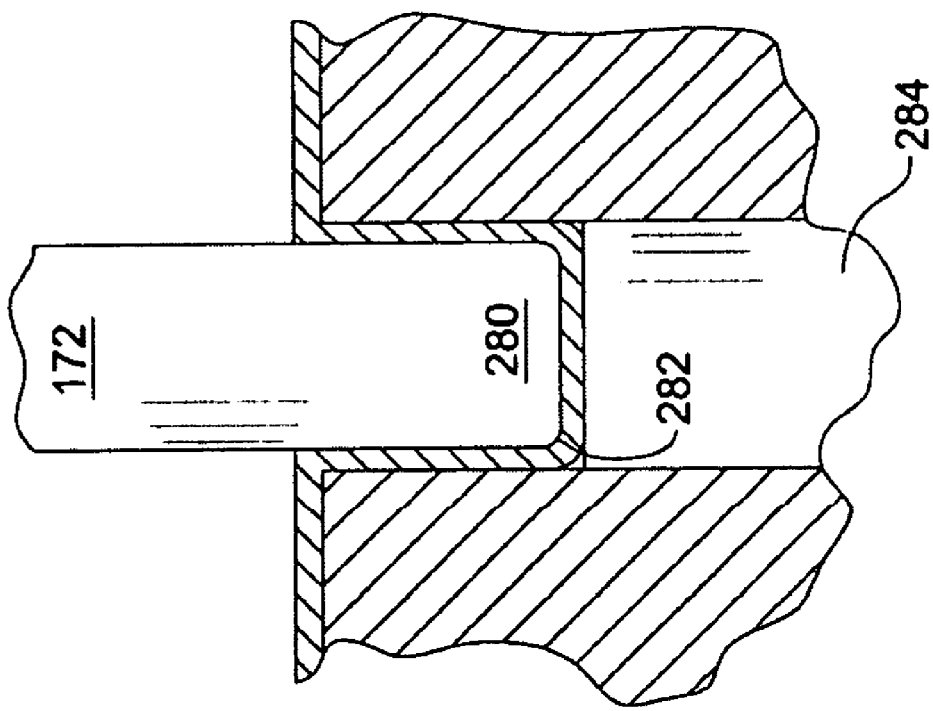
FIG. 10 is a side and partial cross sectional view of how the sixth punch continues the process of the pivot boss formation.

As result of the seventh punching step, pivot boss 74 has an outer wall that rises with near perpendicularity directly from the rest of the metal forming the lower plate 54. The outer circumferential wall of the pivot boss is essentially cylindrical. The top of the boss, seen inverted in FIG. 11, is essentially flat.

In this process, there is minimal surface stressing of the metal forming the boss. The reduction in this stress means that, when the blade base 124 is urged against the pivot boss 74 and is repeatedly pivoted around the boss, the force of these motions are unlikely to cause the metal forming the boss to fail. Further, given that the pivot boss presents a cylindrical surface to the blade base, the force of the blade base against the boss is distributed over a relatively wide area. The heat generated by the motion of the pivoting action is likewise so distributed. The diffusion of this mechanical and thermal energy into the pivot boss 74 likewise serves to minimize the likelihood that the material forming the boss will fail.

Figure 13A:
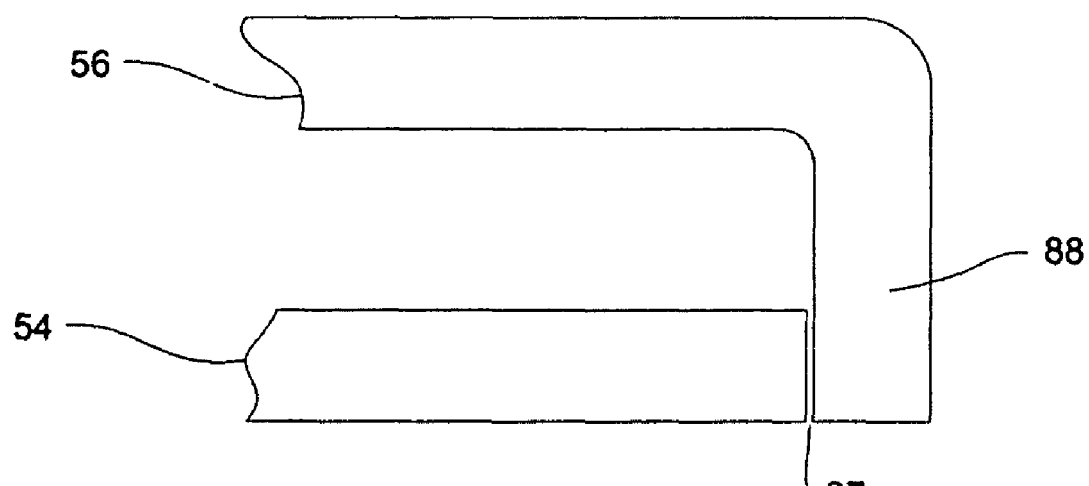
FIG. 13A is a cross sectional view illustrating the gap between the lower and upper plates that form the blade bar prior to the welding of the plates, the gap exaggerated for purposes of illustration.
Figure 12:
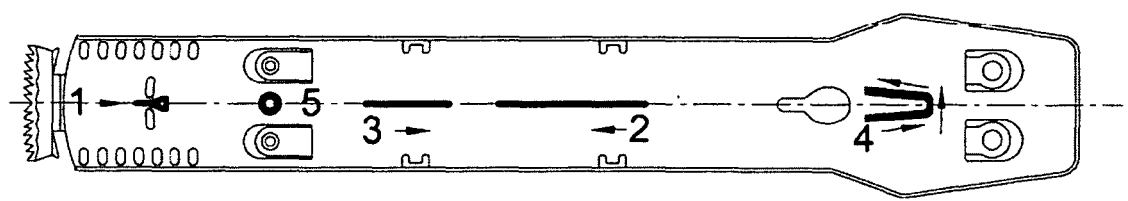
FIG. 12 illustrates the order in which pattern of penetration welds are made on the lower and upper plates forming the blade bar to form the blade bar.
Figure 13:
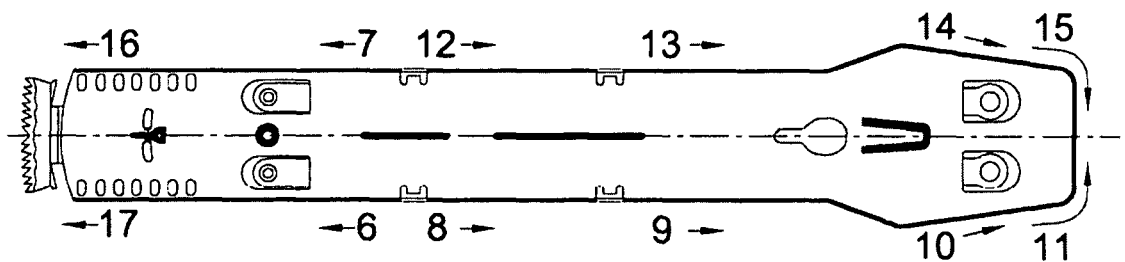
FIG. 13 illustrates the order in which a pattern of welds are formed to weld the opposed edge surfaces of the lower and upper plates together.

It should be appreciated that in each of the punch steps, other processes needed to form the lower plate 54 from the metal ribbon may 158 may be executed. The steps include the overall shaping of the plate from the ribbon, the formation of openings 62, 68, 76, 82, and 84 and the formation of tabs 78. In a separate step or steps (not illustrated), the individual formed lower plates 54 are cut from the lead end of the metal ribbon Once the plates and other components forming saw blade 40 are formed, the components are assembled together. A series of laser welding steps are then used to secure the lower and upper plates 54 and 56, respectively together. FIGS. 12 and 13 illustrate the sequence in which this welding occurs. In a first step, "1" in FIG. 12, a penetration weld through the lower plate 54 is used to weld the inner concealed face of upper plate gusset 106 to the lower plate 54. In the welding, a series of overlapping spot welds are made. Each weld has a diameter of approximately 0.97 mm (0.038 inches). The individual welds are spaced apart approximately 0.33 mm (0.013 inches) from each other.

In the next welding step, "2" in FIG. 12, a series of overlapping penetration spot welds are used to weld a portion of gusset 98 forward of opening 102 to the lower plate 54. This welding starts at a position close to and forward of opening 102 and progresses towards the distal end of the blade bar 44. The whole of the gusset is not so welded to the lower plate in this step. Instead, in a step "3," the lower plate 54 is welded to guest 98 starting at its distal end of the gusset. The weld formed by step "3" stops short of the distal end terminus of the weld formed by step "2".

In the spot welding process of steps "2" and "3" the welds are of the same diameter as in step "1." The welds of steps "2" and "3" are however, more tightly packed, having a separation of approximately 0.20 mm (0.008 inches).

In a step "4," penetration welding is used to form a generally U-shaped weld between the lower plate 54 and the proximal wide end of gusset 98.

In a step "5" a circular weld is formed to weld the lower plate 54 to the perimeter of the top of pivot boss 74. This again is a penetration welding process. In this process, the individual welds have a diameter of approximately 0.84 mm (0.033 inches) are formed. Approximately 40 spot welds are formed over the 360° of the circle to form the weld.

Once the welds are formed along the center of the blade bar 44, welds are formed along the interface where the upper blade lip 88 is adjacent the outer edges of the lower plate 54. Step "6" in FIG. 13 represents the first of these welds. This weld starts at a point distal to the distal most tab 78 on the side of the blade bar and extends forward to a point to the side of one of the openings 84, point 290 in FIG. 13. Step "7" is the formation of the identical weld on the opposed side of the blade bar 44.

Once steps "6" and "7" are executed, two additional welds are formed along side of the blade bar 44 along which the weld of step "6" was formed. In step "8" a weld is formed along the upper plate lip-lower plate interface between the two tabs 78. In step "9" the weld is formed along a line that extends proximally from the proximal most tab 78.

Then, in a step "10" a short weld is formed between two plates along the outer tapered edge of the lower plate base 58. In a step "11" a weld is formed along the base to start a short distance rearward from the proximal end of the weld of step "10". In step "11" the weld is formed around the curve between the side and proximal ends of the lower plate base 58. In each of steps "8," "9," "10," and "11" the welding is performed along a path that moves rearwardly to the proximal end of the blade bar 44.

In a series of steps labeled "12," "13," "14," and "15" in FIG. 13, welds are formed on the opposed side of the blade bar. The welds of steps "12," "13," "14," and "15" correspond to the welds of steps "8," "9," "10," and "11," respectively.

In steps "8" through "15," the individual spots of the overlapping spot welds have a diameter of approximately 0.71 mm (0.028 inches). The centers of the welds are spaced apart approximately 0.32 mm (0.0125 inches).

In a step "16," a weld is formed forward of the weld created step "7." In step "16," the weld is formed to extend to the distal end of the plates 54 and 56. Then in a step "17," a weld is formed on the opposite side of the plates 54 and 56. The weld of step "17" thus extends forward of the weld created in step "6". The spot welds formed in steps "16" and "17" are of the same diameter as those created in steps "8" through "15." However, the welds more closely overlap. The center point spacing between the welds of steps "16" and "17" is approximately 0.061 mm inches).

In order for the welds of steps "6" through "17" to have the desired strength, the outer side edge of the lower bar 54 must be closely located relative to the adjacent inner surface of the lip 88 of the upper bar 56. The gap 87 (FIG. 13A) between these surfaces should be no greater than 0.025 mm (0.001 inches). Ideally, these surfaces should abut.

It should be appreciated that other means may be employed to assemble the blade 40 so that the pivot boss has the desired geometry.

Figure 14A:
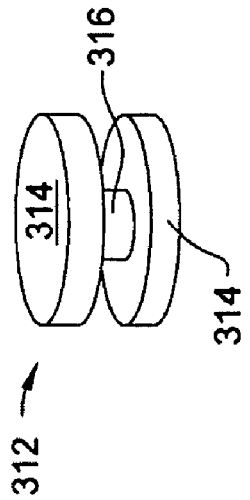
FIG. 14A is a perspective view of an alternative pivot shaft of this invention.
Figure 14B:
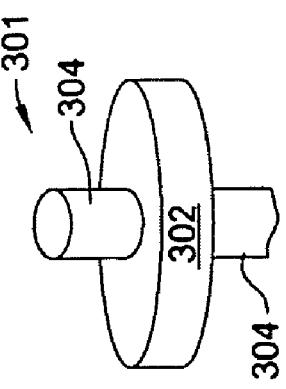
FIG. 14B is a cross sectional view illustrating how the pivot shaft of FIG. 14A is mounted to the blade bar so that the center head of the shaft functions as the blade pivot boss.
Figure 15B:
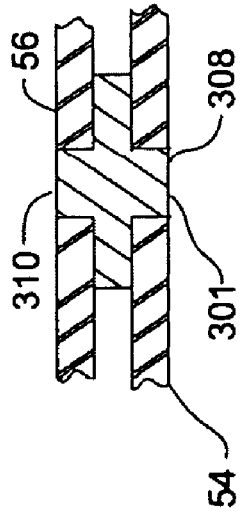
FIG. 15B is a cross sectional view of how the pivot shaft of FIG. 15A is mounted to the blade bar so that the center head of the shaft functions as the blade pivot boss.

For example, the pivot boss could be formed out of a component separate from either the blade bar-forming upper and lower plates 56, 54. FIG. 14A illustrates a pivot shaft 301 that has a disk-shaped head 302. Two cylindrical ears 304 extend outwardly from the opposed faces of the head 302. The ears have a common diameter that is less than the diameter of head 302. As seen in FIG. 14B, when the blade of this version of the invention is assembled, boss ears 304 seat in separate holes 308 and 310 formed in the lower and upper plates 54 and 56, respectively. The ears are welded to the adjacent plates. Pin head 302 functions as the cylindrical member around which the blade head 46 pivots.

In a not illustrated variation of pivot shaft 301, the shaft has a cylindrical head from which a single ear extends. The ear is seated in a through hole in one of the lower or upper plates 54 or 56. The flat face on the other side of the head may be penetration welded to the adjacent surface of the other of the upper or lower plates.

Figure 15A:
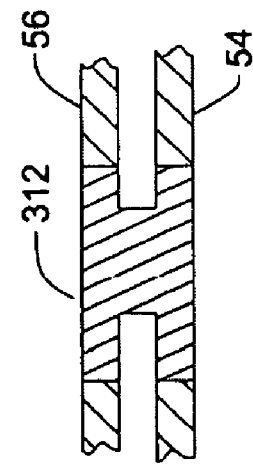
FIG. 15A is a perspective view of an alternative pivot shaft of this invention.

Alternatively, as seen in FIG. 15A, a pivot shaft 312 may have a spindle shape. Shaft 312 has two large diameter disk shaped ears 314. A smaller diameter cylindrical head 316 extends between and connects the ears 314. As seen in FIG.

15B, when a blade with shaft 312 is assembled, head 316 functions as the cylindrical member around which the blade head pivots.

In some versions of the invention, the shaft around which the blade head pivots may be a constant diameter cylindrical pin, (pin not illustrated). The opposed ends of the pin are mounted in aligned openings in the blade bar forming plates.

Figure 16A:
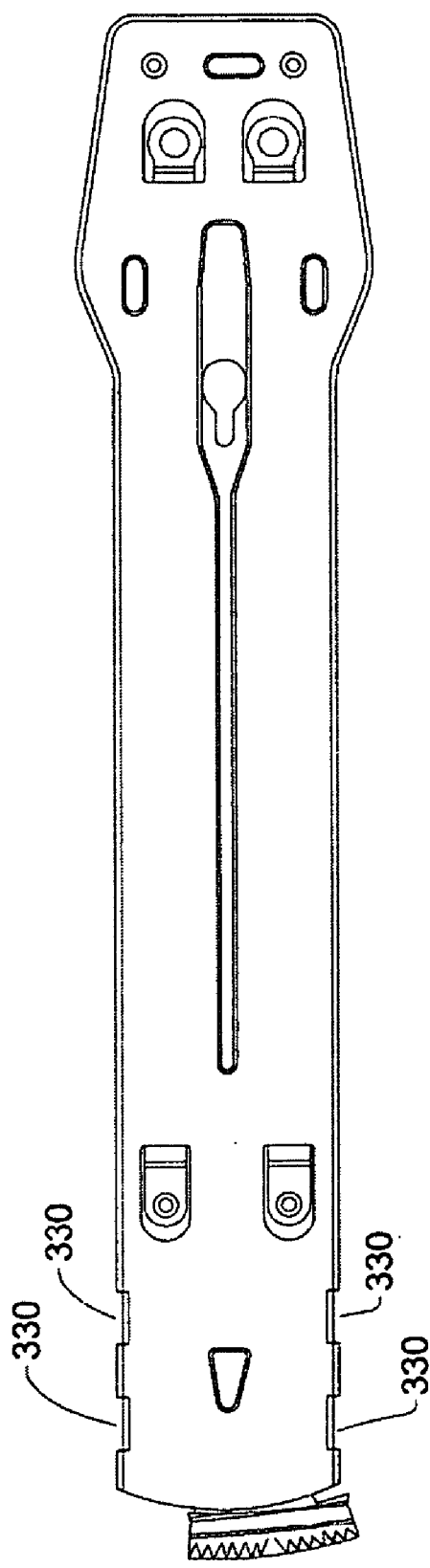
FIG. 16A is a top plan view of an alternative blade assembly of this invention.
Figure 16B:
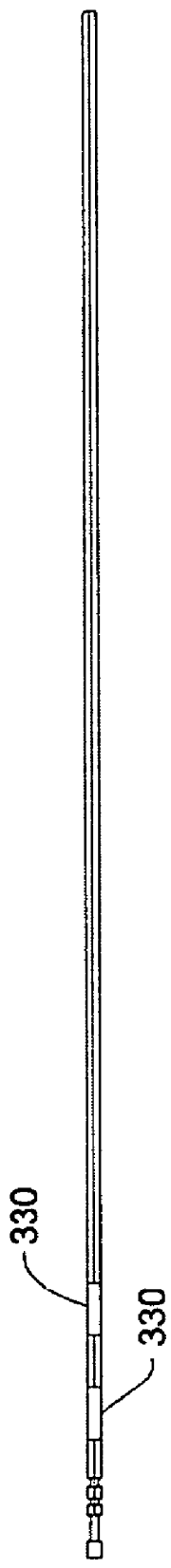
FIG. 16B is a side view of the alternative blade assembly of FIG. 16A.
Figure 17:
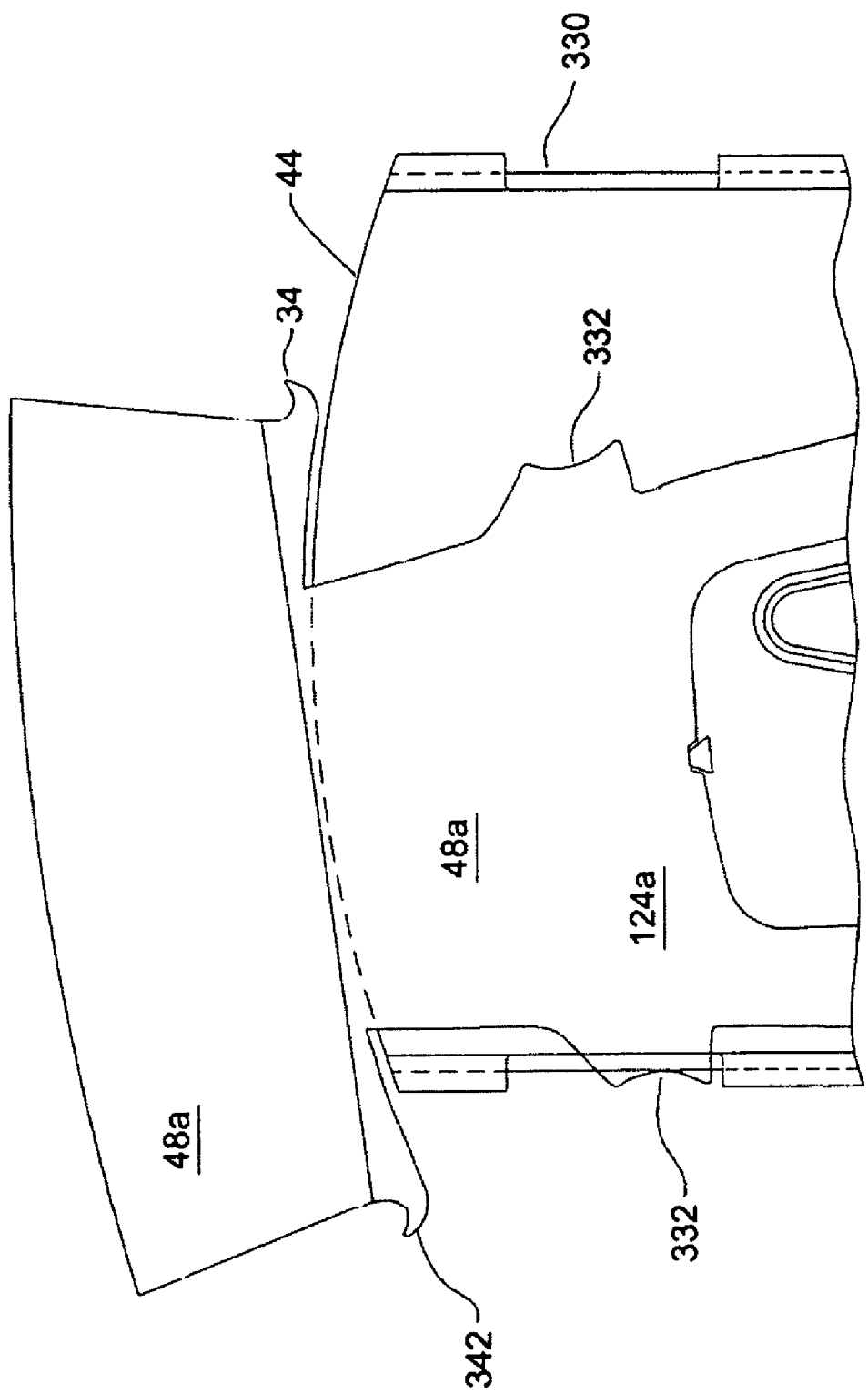
FIG. 17 is a plan view of the blade head integral with the blade assembly of FIG. 16A.

In an alternative version of the blade of this invention, the blade bar 44a is formed with side openings 330, seen in FIGS. 16A and 16B In the version of the invention shown in FIG. 17, the blade has a blade head 46a has a base 124a formed with tabs. Tabs 332, which extend laterally outwardly from the side edges of the base distal section 128a. In the illustrated version of the invention, the outer sides of tabs 332 have a concave profile. It should be understood that this is illustrative, not limiting. In some versions of the invention, the tabs have a triangular profile. That is, each tab has a face that tapers outwardly from the base distal section from which it extends. Then at the widest most proximal position, the tab has an edge that meets the distal section at an angle equal to or close to a right angle. In still another version of this invention, the outer edge of each tab 332 is a straight edge. While not illustrated, it should be appreciated that similar tabs extend outwardly from the base proximal section.

These tabs are positioned so that, when the blade head 46a pivots to one side of the blade bar 44, the tabs extend out of the adjacent openings 330. Thus, the tabs function as plows that push debris trapped in the blade bar out of the blade bar. The ejection of debris minimizes the likelihood that the debris will clog in the blade bar and adversely affect operation of the blade FIG. 17 also illustrates a blade head crown 48a that has an arcuate shape. Thus the opposed side edges 340 of the crown lie on spaced apart radial lines that project from a common center point. Blade head crown 48a is further formed to have, at the proximal ends of the crown, outwardly projecting fingers 342. Each finger 342 extends outwardly from the associated side edge. Each finger is generally J-shaped and oriented so that the hooked end of the finger extends in the forward direction, towards radius along which the distal ends of the blade teeth lie.

When a blade with blade head crown 48a is actuated, fingers 342 push debris trapped in the kerf formed by the blade teeth out of the path of travel of the crown 48a. This displacement of the debris reduces the extent to which the debris may reduce cutting efficiency and be displaced rearwardly where they can become entrained in the blade bar.

Figure 18:
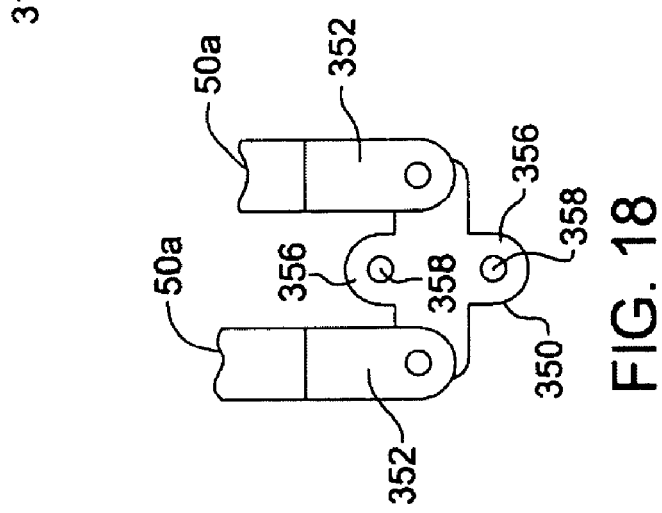
FIG. 18 is a plan view of the distal end of two drive rods and the connecting foot of another blade assembly of this invention.

FIG. 18 illustrates an alternative construction of portion of the blade assembly of this invention. Specifically, FIG. 18 illustrates how a planar drive foot 350 may be coupled to the proximal end of the blade assembly drive rods 50a. In this version of the invention, overlapping fingers 352, similar to fingers 142 (FIG. 2) extend proximally rearward from each drive rod 50a. Drive foot 350 has opposed outwardly extending tabs 354. Each tab 354 is pivotally fitted into the slot defined by a pair of the overlapping drive rod fingers 352.

Foot 350 also has two opposed tabs 356 that are nominally oriented along the longitudinal axis of the blade assembly. Each tab 356 has an opening 358. This blade assembly of this invention is for attachment to a handpiece with a drive head with two drive pins that are nominally aligned with the longitudinal axis of the handpiece. When the drive pins oscillate, they cause the foot 350 to undergo a like motion. This motion reciprocates the drive rods 50a back and forth so as to cause the desired blade head pivotal movement.

Alternatively, foot 350 is formed with a center hole that is not circular in profile. The blade of this version of the invention is attached to a handpiece with a single drive pin. The drive pin has a cross sectional geometry that allows the pin to be closely slip fitted in the complementary hole in the blade foot 350. When the handpiece is actuated, the drive pin oscillates. This motion results in a like movement of the foot 350. Foot 350 transfers to the oscillatory motion to the drive rods 50a so that the drive rods reciprocate.

Thus it should be understood that the foregoing is directed to specific features of the blade and method of manufacture of this invention. The invention may vary from what has been described.

For example there is no requirement that the method of pivot boss formation by punching and the method of laser welding the bar-forming lower and upper plates be practiced in all versions of this invention. These methods, when appropriate may be practiced separately.

In the method of pivot boss formation by punching of this invention, fewer or more steps may be needed to form that pivot boss so that it has the desired geometry and to ensure that the material from which it is formed has the desirable stress free surface finish.

Alternative means may be employed to form the pivot boss. For example, it may be possible to form the pivot boss, as well as the rest of the plate with which the pivot boss is integral, by selective etching a blank workpiece. As a result of this etching at least the pivot boss, if not other features of the blade plate, develop the desired shape. Also, in some versions of the invention, the outer wall of the pivot boss may not have the completely circular cross sectional profile.

Alternative sequences of laser welding the lower and upper plates together in accordance with this invention may also be practiced.

Further, in some versions of the invention, processes other than laser welding may be performed to form the desired welds. Thus, in some versions of this invention arc welding, split electron beam or resistance welding may be used to form the center welds of the gussets and/or the welding of the sides of the upper and plates 54 and 56, respectively, together.

Therefore, it is an object of the appended claims to cover all such variations and modifications that come within the true spirit and scope of this invention.

What is claimed is:

1. A method of assembling a surgical sagittal saw blade assembly having an oscillating blade head, said method including the steps of:
   providing a first plate;
   punching out a portion of said first plate to form a boss, said boss having an outer wall that is at least partially circular and a top surface that is substantially perpendicular to said outer wall;
   positioning a blade head on a distal end of said first plate, said blade head having a base that is disposed against said boss so as to be able to pivot around said outer wall of said boss and a crown located outside of said first plate, the crown being formed with teeth;
   positioning at least one drive rod on said first plate, said at least one drive rod attached to said blade head; and
   securing a second plate to said first plate to form a blade bar having an opening from which said blade head crown extends.

2. The method of claim 1, wherein said punching step to define said boss includes performing a plurality of different punching sub-steps that are sequentially performed to form said boss.

3. The method of claim 1, wherein, as a result of said punching out a portion of said first plate to form said boss, the outer wall of said boss has a substantially circular shape.

4. The method of claim 1, wherein said securing step includes welding said first plate and said second plate together to form said blade bar.

5. The method of claim 4, wherein said welding step includes the steps of:
forming at least one center weld between said plates, said center weld located inwardly of opposed sides of said plates; and
after said at least one center weld is formed, welding together a first section of adjacent surfaces on a first side of said plates; welding together a first section of adjacent surfaces on a second side of said plates; welding together a second section of adjacent surfaces on said first side of said plates; and welding together a second section of adjacent surfaces on said second side of said plates.

6. The method of claim 5, wherein at least one of said step of forming at least one center weld between said plates or said step of welding of said sides of said plates is performed by laser welding.

7. The method of claim 5, wherein said step of forming at least one center weld is performed by penetration welding opposed adjacent interior surfaces of said plates together.

8. The method of claim 1, wherein said securing step further includes welding said top surface of said boss to an interior surface of said second plate.

9. The method of claim 1, wherein said steps of securing said second plate to said first plate to form said blade bar includes the steps of:
forming at least one inwardly directed gusset in one of said plates; and
forming at least one center weld between said plates, wherein the at least one said gusset is welded to an adjacent interior surface of a second one of said plates.

10. The method of claim 1, wherein said method further includes:
forming one of said first plate or said second plate with a lip that extends along an outer perimeter of said plate so that when said first plate and said second plate are placed together, a side edge surface the other plate is adjacent a side surface of said lip; and
said securing step includes welding said plates together so that the side surface of said lip is welded to the other one of the plates.

11. A method of assembling a surgical sagittal saw blade having an oscillating blade head, said method including the steps of:
providing a first plate;
providing a boss on said first plate, said boss having an outer wall that is at least partially circular and a top surface that is substantially perpendicular to said outer wall;
positioning a blade head on a distal end of said first plate, said blade head having a base that is disposed against said boss so as to be able to pivot around said outer wall of said boss and a crown located outside of said first plate, said crown being formed with teeth;
positioning at least one drive rod on said first plate, said at least one drive rod attached to said blade head;
disposing an opposed second plate over said first plate, said blade head base and said at least one drive rod, said plates having opposed longitudinally extending sides; and
welding said first and second plates together to form a blade bar, said blade bar having a distal end opening from which said blade head crown extends;
wherein said welding step is performed by:
forming at least one center weld between said plates, said center weld located inwardly of said opposed sides of said plates; and
after said at least one center weld is formed, welding together a first section of adjacent surfaces on a first side of said plates; welding together a first section of adjacent surfaces on a second side of said plates; welding together a second section of adjacent surfaces on said first side of said plates; and welding together a second section of adjacent surfaces on said second side of said plates.

12. The method of assembling a surgical saw blade having an oscillating blade head of claim 11, wherein at least one of said step of forming at least one center weld between said plates or said step of welding of said sides of said plates is performed by laser welding.

13. The method of assembling a surgical saw blade having an oscillating blade head of claim 11, wherein said step of forming at least one center weld is performed by penetration welding opposed adjacent interior surfaces of said plates together.

14. The method of assembling a surgical saw blade having an oscillating blade head of claim 11, wherein said method further includes the steps of:
forming at least one inwardly directed gusset in one of said plates, said at least one gusset being located inwardly of the opposed sides of the plate; and
in said step of forming at least one center weld between said plates, said at least one gussets is welded to an adjacent interior surface of a second one of said plates.

15. The method of assembling a surgical saw blade having an oscillating blade head of claim 11, wherein said method further includes:
forming one of said first plate or said second plate with a lip that extends along an outer perimeter of said plate so that when said first plate and said second plate are placed together, a side edge surface the other plate is adjacent a side surface of said lip; and
said securing step further includes welding said plates together so that the side surface of said lip is welded to the other one of said plates.

16. The method of assembling a surgical sagittal saw blade having an oscillating blade head of claim 11, wherein said step of providing the boss on said first plate is performed by punching out a portion of said first plate to form said boss.

17. The method of assembling a surgical sagittal saw blade having an oscillating blade head of claim 11, wherein, in said step of positioning a blade head on the distal end of said first plate, the base and the crown of the blade head positioned on said first plate each have a thickness and the thickness of the crown is greater than the thickness of the blade head base.

18. The method of assembling a surgical saw blade having an oscillating blade head of claim 11, wherein:
at least one of said plates is provided with an opening that is located proximal to a distal end of said plate;
said at least one drive rod has at a distal end of said drive rod a finger that extends above and distally forward of said drive rod wherein said finger extends over and is moveably attached to said blade head base; and
as a result of said positioning said at least one drive rod on said first plate or said securing said second plate to said first plate, said drive rod finger seats in the opening formed in the at least one said plate.

19. The method of assembling a surgical saw blade having an oscillating blade head of claim 11, wherein, in said step of positioning at least one drive rod on said first plate, plural drive rods are positioned on said first plate, each said drive rod being attached to said blade head.

20. The method of assembling a surgical sagittal sagittal saw blade assembly of claim 1, wherein, in said step of positioning a blade head on the distal end of said first plate, the base and the crown of the blade head is positioned on said first plate each have a thickness and the thickness of the crown is greater than the thickness of the blade head base.

21. The method of assembling a surgical sagittal saw blade assembly of claim 1, wherein:
at least one of said plates is provided with an opening that is located proximal to a distal end of said plate;
said at least one drive rod has at a distal end of said drive rod a finger that extends over above and distally forward of said drive rod where said finger extends over and is moveably attached to said blade head base; and
as a result of said positioning said at least one drive rod on said first plate or said securing said second plate to said first plate, said drive rod finger seats in the opening formed in the at least one said plate.

22. The method of assembling a surgical sagittal saw blade assembly of claim 1, wherein, in said step of positioning at least one drive rod on said first plate, plural drive rods are positioned on said first plate, each said drive rod being attached to said blade head.

* * * * *